(12) United States Patent
Zhang et al.

(10) Patent No.: US 11,938,465 B2
(45) Date of Patent: Mar. 26, 2024

(54) COORDINATION ZIRCONIUM PHOSPHOTUNGSTATE CATALYST AND ITS APPLICATION IN CATALYTIC HYDROGENATION OF FURFURAL

(71) Applicant: JIANGNAN UNIVERSITY, Jiangsu (CN)

(72) Inventors: Liping Zhang, Jiangsu (CN); Haijun Wang, Jiangsu (CN); Guangzhi Xu, Jiangsu (CN); Chen Liu, Jiangsu (CN)

(73) Assignee: JIANGNAN UNIVERSITY, Jiangsu (CN)

(*) Notice: Subject to any disclaimer, the term of this patent is extended or adjusted under 35 U.S.C. 154(b) by 868 days.

(21) Appl. No.: 16/971,775

(22) PCT Filed: Mar. 18, 2019

(86) PCT No.: PCT/CN2019/078471
§ 371 (c)(1),
(2) Date: Aug. 21, 2020

(87) PCT Pub. No.: WO2020/186421
PCT Pub. Date: Sep. 24, 2020

(65) Prior Publication Data
US 2021/0031173 A1    Feb. 4, 2021

(51) Int. Cl.
*B01J 27/188*    (2006.01)
*B01J 37/04*    (2006.01)
(Continued)

(52) U.S. Cl.
CPC ............. *B01J 27/188* (2013.01); *B01J 37/04* (2013.01); *B01J 37/06* (2013.01); *B01J 37/343* (2013.01); *C01B 25/45* (2013.01); *C07D 307/44* (2013.01)

(58) Field of Classification Search
CPC . B01J 27/188; B01J 37/04; B01J 37/06; B01J 37/343; B01J 31/18; B01J 35/002; C01B 25/45; C07D 307/44
See application file for complete search history.

(56) References Cited

U.S. PATENT DOCUMENTS
2017/0320790 A1    11/2017 Hwang et al.

FOREIGN PATENT DOCUMENTS
CN    102066301 A    5/2011
CN    102764664 A    11/2012
(Continued)

OTHER PUBLICATIONS
Winoto et al (Heteropolyacid supported on Zr-Beta zeolite as an active catalyst for one-pot transformation of furfural to γ-valerolactone, Applied Catalysis B: Environmental, 2019) (Year: 2019).*
(Continued)

*Primary Examiner* — Samir Shah
*Assistant Examiner* — Logan Edward Laclair
(74) *Attorney, Agent, or Firm* — HAUPTMAN HAM, LLP

(57) ABSTRACT

The invention discloses a coordination type zirconium phosphotungstate catalyst and its application in catalytic hydrogenation of furfural, belonging to the field of heterogeneous catalysis. The zirconium phosphotungstate catalyst prepared by the invention not only has good catalytic effect on the conversion of furfural to furfuryl alcohol, but also has mild reaction conditions. The yield of solid line furfuryl alcohol can be 98% if it can be reacted for 1 h at 120 ° C., and the amount of catalyst is less, which greatly reduces the energy consumption in the prior art. In addition, the zirconium phosphotungstate prepared by the invention is easy to sepa-
(Continued)

rate, has good stability for catalyzing the hydrogenation of furfural to furfuryl alcohol, and is a new, efficient and green catalyst.

10 Claims, 4 Drawing Sheets

(51) Int. Cl.
    *B01J 37/06*     (2006.01)
    *B01J 37/34*     (2006.01)
    *C01B 25/45*     (2006.01)
    *C07D 307/44*     (2006.01)

(56) References Cited

FOREIGN PATENT DOCUMENTS

| CN | 105645372 A | 6/2016 |
|---|---|---|
| CN | 106008207 A | 10/2016 |
| CN | 108276364 A | 7/2018 |
| CN | 108295878 A | 7/2018 |

OTHER PUBLICATIONS

International Search Report dated Dec. 9, 2019 for related PCT/CN2019/078471 filed Mar. 18, 2019.
Written Opinion dated Dec. 9, 2019 for related PCT/CN2019/078471 filed Mar. 18, 2019.

* cited by examiner

COORDINATION ZIRCONIUM PHOSPHOTUNGSTATE CATALYST AND ITS APPLICATION IN CATALYTIC HYDROGENATION OF FURFURAL

RELATED APPLICATIONS

This is a U.S. national stage of international application No. PCT/CN2019/078471 filed on Mar. 18, 2019.

BACKGROUND OF THE INVENTION

1. Technical Field

The invention relates to a coordination type zirconium phosphotungstate catalyst and its application in catalytic hydrogenation of furfural, belonging to the field of heterogeneous catalysis.

2. Background Art

With the rapid development of society, the supply of fossil energy is in short supply, the over exploitation and waste of resources, so the search for new, green and renewable energy has received extensive attention. Biomass is not only a kind of renewable resource, but also the most widely distributed, numerous and diverse energy on the earth, so it has attracted great attention of many researchers. Through the basic material platform of biomass, more and more high value-added compounds are produced with these basic materials as raw materials, so the development of new production technology, production routes, and the production of high value-added compounds have a profound impact on the actual production and the development of modern industry.

Furfural, as the basic platform material of biomass, is a kind of five carbon compound, derived from some agricultural products such as wheat, corncob and so on. It has rich reserves and a wide range of uses. Furfural can be used as a basic raw material to synthesize many high value-added compounds, among which furfuryl alcohol is a high value-added compound. Furfural alcohol can be used in the production of resin, fuel, synthetic fiber, rubber, plastic, pesticide and other industries.

However, at present, the industrial production route of hydrogenation of furfural to furfuryl alcohol is still under high temperature and high hydrogen pressure. The traditional fossil energy derived from petroleum is used, and the reaction conditions are relatively harsh, which brings great burden on energy and economy. In recent years, there have been many reports about the synthesis of furfuryl alcohol from furfural with the presence of coordination catalyst. However, the reaction conditions of the preparation methods in these reports are still relatively harsh, many of which need to be carried out at a temperature higher than 120° C. or under hydrogen, or at a temperature lower than 120° C. for a long time. For example, cn107445923a discloses a process for preparing furfuryl alcohol by hydrogenation of furfural, which uses copper supported polyglutamic acid/N-hydroxymethylacrylamide as catalyst and hydrogen as hydrogen source. Cn107963998a discloses the method of furfural formic acid transfer hydrogenation to furfuryl alcohol. With Pd/C and CuO as composite catalyst and formic acid as hydrogen donor, it needs to react at 170° C. for 3 hours to obtain better catalytic effect.

Therefore, it is necessary to find a new catalyst to solve the problems in the existing technology, such as the use of $H_2$, higher reaction temperature or Pd.

Phosphotungstic acid is a new multifunctional catalyst with high catalytic activity and good stability. It can be used for homogeneous and heterogeneous reactions. It is mainly used as catalyst, biochemical reagent and chromatographic analysis reagent for organic synthesis reaction. As a catalyst, phosphotungstic acid has the advantages of high activity, green and pollution-free, can be recycled for many times, and less activity loss.

SUMMARY OF THE INVENTION

Technical Issues

In the prior art, the reaction conditions for hydrogenation of furfural to furfuryl alcohol are harsh and the use of precious metals is also a problem.

Technical Proposal

In order to solve the problems in the prior art, such as the harsh reaction conditions for the hydrogenation of furfural to furfuryl alcohol and the use of precious metals, the invention provides a coordination type zirconium phosphotungstate catalyst with high catalytic capacity. In the process of catalytic conversion of furfural to furfural alcohol, the yield of furfural alcohol reacts at 120° C. 1 h can reach 98%, which can achieve high catalytic activity under mild reaction conditions and is easy to recycle.

Specifically, the invention first provides the preparation method of the coordination type zirconium phosphotungstate catalyst, the method includes the following steps: dissolve phosphotungstic acid and $ZrCl_4$ in DMF respectively, after ultrasonic treatment, add the phosphotungstic acid solution drop by drop into $ZrCl_4$ solution within 5-30 min, after uniform mixing, add triethylamine, then react at room temperature for 3-6 h, aging time is more than 4 h, respectively use DMF The coordination zirconium phosphotungstate catalyst was obtained by washing 1-3 times with methanol and anhydrous ether and drying in vacuum at 70-100° C. for more than 8 hours.

In one embodiment of the invention, the ultrasonic processing time is 5-30 min, and the ultrasonic frequency is 40-60 kHz.

In one embodiment of the invention, the molar ratio of the phosphotungstic acid and $ZrCl_4$ is 3:1~1:3.

In one embodiment of the invention, the concentration of phosphotungstic acid is (0.05-0.15) mol/L, and the concentration of $ZrCl_4$ is (0.05-0.15) mol/L.

In one embodiment of the invention, the addition amount of the triethylamine is 1-3 ml/mmol phosphotungstic acid.

Secondly, the invention also provides a coordination type zirconium phosphotungstate catalyst prepared by the preparation method.

Moreover, the invention provides a method for catalyzing the hydrogenation of furfural to prepare furfuryl alcohol. Taking the coordination zirconium phosphotungstate prepared by the above method as the catalyst, furfural as the substrate, and adding 0.01-0.03 g coordination zirconium phosphotungstate/mmol furfural as the catalyst, the reaction takes place at 110-150° C. for 0.5-4 h, wherein isopropanol is used as the hydrogen source, and the addition amount is 5-10 ml/mmol furfural.

In one embodiment of the invention, the reaction temperature is preferably 120° C.

In one embodiment of the invention, the reaction time is preferably 1 h.

In one embodiment of the invention, the amount of isopropanol added is 5 ml/mmol furfural.

In one embodiment of the invention, the addition amount of coordination type zirconium phosphotungstate is preferably 0.02 g/mmol furfural.

Finally, the invention also provides the application of the catalytic hydrogenation of furfural to furfuryl alcohol in the preparation of resin, fuel, synthetic fiber, rubber, plastic and pesticide.

Compared with the prior art, the invention has the following advantages and effects:

(1) The catalyst used in the invention is coordination type zirconium phosphotungstate, which not only has good catalytic effect on the conversion of furfural to furfural alcohol, but also has mild reaction conditions. The yield of solid line furfural alcohol can be 98% after reacting for 1 h at 120° C., greatly reducing the energy consumption in the prior art.

(2) The raw material phosphotungstic acid selected for the catalyst of the invention has a special structure, which can provide a good micro environment for the reaction, thus improving the yield and selectivity of furfural alcohol; the active part of the catalyst used in the invention is metal zirconium, which has good properties, and realizes the efficient conversion of furfural to furfural alcohol under relatively mild reaction conditions.

(3) The coordination type zirconium phosphotungstate catalyst of the invention is heterogeneous. After the reaction, the catalyst can be recovered and used in the next reaction through simple filtration, and still has good catalytic effect after multiple cycles, which embodies the policy of green chemistry.

DESCRIPTION OF PREFERRED EMBODIMENTS

Figure 1:
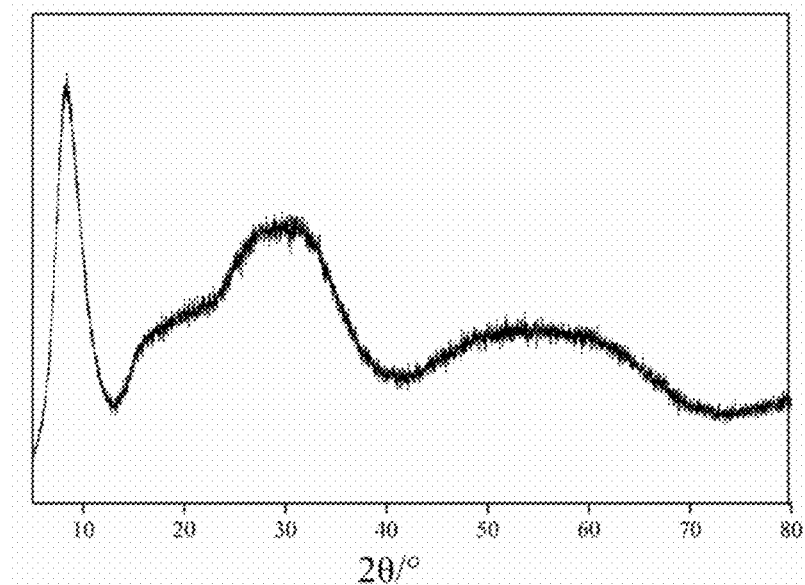
FIG. 1 is the XRD diagram of the coordination zirconium phosphotungstate catalyst prepared in example 1.

Determination of furfural by gas chromatography (GC): calculate the ratio of peak area of furfural (FF) and furfuryl alcohol (FA), with naphthalene as reference sample.

Calculation formula of conversion rate:

$$FF \text{ conversion (mol \%)} = \left(1 - \frac{\text{moles of } FF}{\text{initial moles of } FF}\right) \times 100\%. \quad (1)$$

Calculation formula of yield:

$$\text{Yield of } FA \text{ (mol \%)} = \left(\frac{\text{moles of } FA}{\text{initial moles of } FF}\right) \times 100\%. \quad (2)$$

The invention will be further described in combination with embodiments, but the embodiments of the invention are not limited to this.

EXAMPLE 1

(1) Pretreatment of raw materials: the phosphotungstic acid containing crystal water is dried in vacuum at 100° C. for 10h, and then it is ground into powder in a mortar.

(2) Preparation of zirconium phosphotungstate (Zr—PW): take 2.88 g of the pretreated phosphotungstic acid, dissolve it in DMF, the concentration of phosphotungstic acid is 0.05 mol/l, and treat it in ultrasonic for 20 min, then take 0.466 g of $ZrCl_4$, dissolve it in DMF, the concentration of $ZrCl_4$ is 0.1 mol/l, and treat it in ultrasonic for 20 min. Put the ultrasonic treated $ZrCl_4$ solution into a round bottom flask and add the ultrasonic treated phosphotungstic acid solution drop by drop within 30 minutes. After the above solution is uniformly mixed, add 3 ml triethylamine solution drop by drop, react at room temperature for 4 h, age for 4 h, wash with DMF, methanol and anhydrous ether for three times respectively, dry in vacuum at 80° C. for 12 h, and grind it to powder to prepare zirconium phosphotungstate (Zr—PW).

Figure 2:
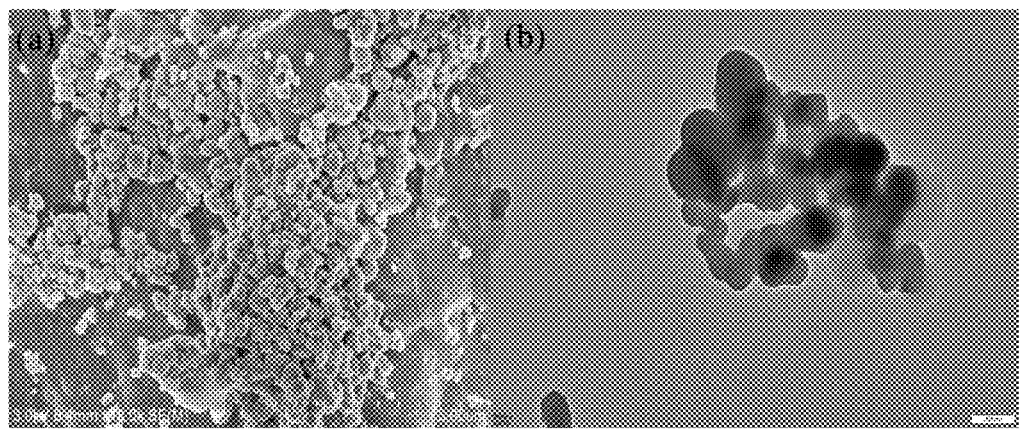
FIG. 2 is the SEM (left) and TEM (right) photos of the coordination zirconium phosphotungstate catalyst prepared in example 1.

The prepared zirconium phosphotungstate (Zr—PW) is characterized by its XRD and electron micrographs as shown in FIG. 1 and FIG. 2, respectively. It can be seen that the catalyst prepared by the invention is an irregular mesoporous structure.

EXAMPLE 2

(1) Pretreatment of raw materials: the phosphotungstic acid containing crystal water is dried in vacuum at 100° C. for 10 h, and then it is ground into powder in a mortar.

(2) Preparation of zirconium phosphotungstate (Zr—PW): take 2.88 g of the pretreated phosphotungstic acid and dissolve it in DMF, the concentration of phosphotungstic acid is 0.10 mol/l, and then deal with it in ultrasonic for 15 min, then take 0.466 g of $ZrCl_4$ and dissolve it in DMF, the concentration of $ZrCl_4$ is 0.10 mol/l, and deal with it in ultrasonic for 20 min. Put the ultrasonic treated $ZrCl_4$ solution into a round bottom flask and add the ultrasonic treated phosphotungstic acid solution drop by drop within 20 minutes. After the above solution is evenly mixed, add 3 ml triethylamine solution drop by drop, react at room temperature for 3 h, age for 5 h, wash with DMF, methanol and anhydrous ether for three times respectively, dry in vacuum at 100° C. for 10 h, grind it to powder to prepare zirconium phosphotungstate (Zr—PW).

EXAMPLE 3

(1) Pretreatment of raw materials: the phosphotungstic acid containing crystal water is dried in vacuum at 100° C. for 10 h, and then it is ground into powder in a mortar.

(2) Preparation and catalytic performance of zirconium phosphotungstate (Zr—PW) with different ratio: $ZrCl_4$: PW (phosphotungstic acid) with the molar ratio of 3:1, 2:1, 1:1, 1:2 and 1:3 was used to synthesize zirconium phosphotungstate. The two raw materials were respectively dissolved in 20 ml DMF and treated with ultrasonic for 20 min. After the above solution is evenly mixed, add 3 ml triethylamine solution drop by drop, react at room temperature for 4 h, age for 4 h, wash with DMF, methanol and anhydrous ether for three times respectively, dry in vacuum at 80° C. for 12 h, grind it to powder to prepare zirconium phosphotungstate catalyst.

The prepared zirconium phosphotungstate catalyst was used as the catalyst for furfural:

(1) Weigh 200 mg of the above catalyst into 20 ml of polytetrafluoroethylene lining respectively, add quantitative naphthalene (here naphthalene as reference sample, the same below) and 5 ml of isopropanol;

(2) Weigh 0.1 mol furfural and add it into the system in step (1), put the PTFE lining into the stainless steel reactor, heat it to 150° C. under magnetic stirring, and react for 3 hours. After the reactor cools to room temperature, use the centrifuge to separate the solid and liquid, and take the liquid phase test sample;

(3) Transfer 50 μL of reaction solution in step (2) with a pipette gun, and determine the yield of furfuryl alcohol with a liquid chromatograph.

TABLE 1 catalytic performance of zirconium phosphotungstate catalysts with different proportions

| proportion | 3:1 | 2:1 | 1:1 | 1:2 | 1:3 |
|---|---|---|---|---|---|
| $C_{FF}$ | 100 | 92.3 | 90.03 | 100 | 99.14 |
| $Y_{FA}$ | 35 | 58.37 | 40.24 | 39.86 | 42.22 |

It can be seen that zirconium phosphotungstate prepared by $ZrCl_4$: PW (phosphotungstic acid) with the molar ratio of 2:1 is selected as the catalyst for further study.

EXAMPLE 4

According to the method of example 1, $ZrCl_4$ is replaced with $AlCl_3$ to prepare the corresponding catalyst aluminum phosphotungstate (Al—PW); in addition, according to the method of example 1, the catalyst phosphotungstic acid and $ZrCl_4$ are separately prepared with phosphotungstic acid and $ZrCl_4$ as reaction raw materials.

According to the method of example 1, phosphotungstic acid is replaced by phosphomolybdic acid (PM), which is reacted with $ZrCl_4$ and $AlCl_3$ respectively to prepare corresponding catalysts zirconium phosphomolybdate (Zr—PM) and aluminum phosphomolybdate (Al—PM). In addition, the catalyst phosphomolybdic acid is separately prepared with phosphomolybdic acid according to the method of example 1.

The catalyst Zr—PW prepared in example 1 and the catalyst Al—PW, phosphotungstic acid, $ZrCl_4$, zirconium phosphomolybdate Zr—PM, aluminum phosphomolybdate Al—PM or phosphomolybdate PM prepared in example 4 were used as catalysts for furfural respectively (1) Weigh 200 mg of the above catalysts (Zr—PW, Al—PW, phosphotungstic acid, $ZrCl_4$, Zr—PM, Al—PM or PM) respectively into 20 ml of polytetrafluoroethylene lining, add quantitative naphthalene (here naphthalene as reference sample, the same below) and 5 ml of isopropanol;

(2) Weigh 0.1 mol furfural and add it into the system in step (1), put the PTFE lining into the stainless steel reactor, heat it to 120° C. under magnetic stirring, and react for 1 h. After the reactor cools to room temperature, use the centrifuge to separate the solid and liquid, and take the liquid phase test sample;

(3) Transfer 50 μL of reaction solution in step (2) with a pipette gun, and determine the yield of furfuryl alcohol with a liquid chromatograph.

Figure 3:
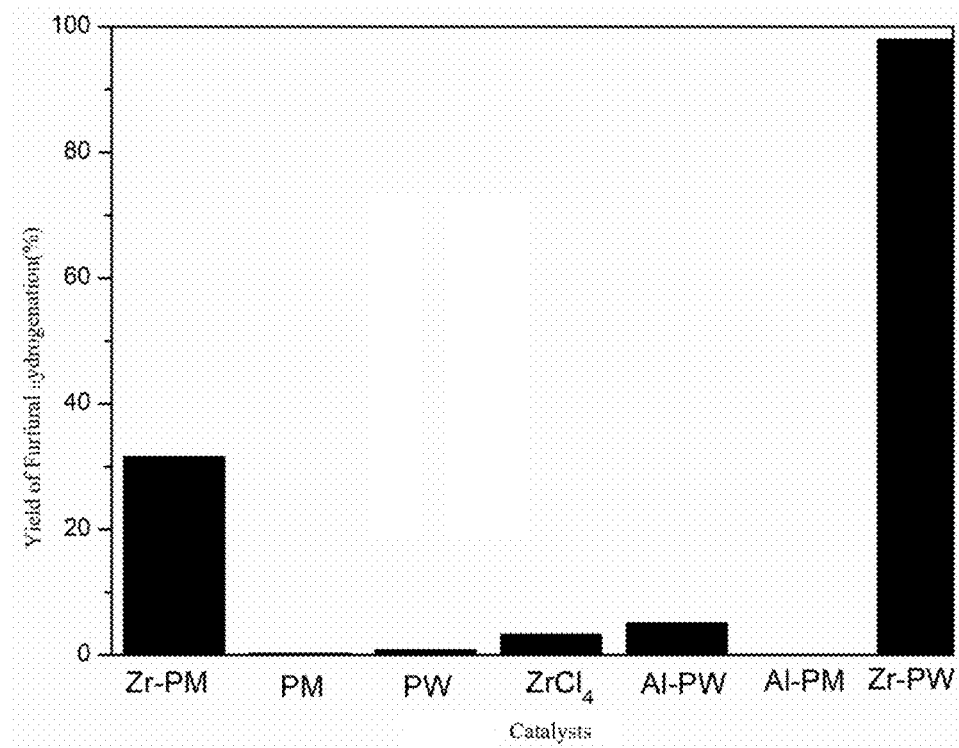
FIG. 3 shows the furfuryl alcohol yield of Furfural Hydrogenation Catalyzed by different types of zirconium phosphotungstate catalysts in example 4.

According to the determination, the results are as shown in FIG. 3. The catalysts prepared from Zr—PM, PM, PW, $ZrCl_4$, Al—PW, Al—PM or Zr—PW are used to catalyze the hydrogenation of furfural. The yields of furfural are 31.56%, 0.32%, 0.81%, 3.26%, 5.11%, 0% and 98.64% respectively. It can be seen that only Zr PW catalyst has good catalytic performance for furfural production.

EXAMPLE 5

(1) Weigh 200 mg of coordination zirconium phosphotungstate prepared in example 1 into 20 ml of polytetrafluoroethylene lining, and add quantitative naphthalene and 5 ml of isopropanol;

(2) Weigh 0.1 mol furfural and add it into the reaction system of step (1), put the PTFE lining into the stainless steel reactor, heat it to 110° C.~150° C. under magnetic stirring, and react for 1H. After the reaction is finished, after the reactor cools to room temperature, separate the solid and liquid with centrifuge, and take the liquid phase test sample;

(3) Transfer 50 μL of reaction solution in step (2) with a pipette gun, and determine the yield of furfuryl alcohol with a liquid chromatograph.

Figure 4:
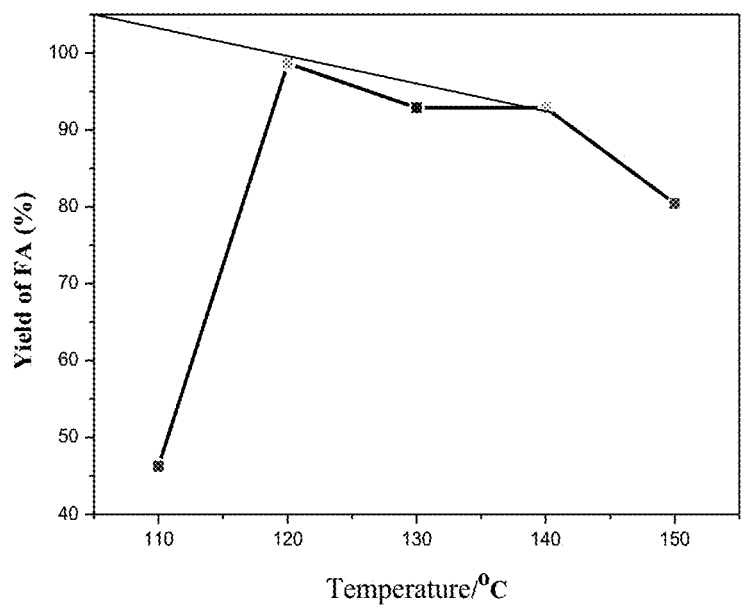
FIG. 4 shows the furfuryl alcohol yield of the coordinated zirconium phosphotungstate catalyst in example 5 under different temperatures.

As shown in FIG. 4, when the reaction temperature is 110° C., 120° C., 130° C., 140° C. and 150° C., the yield of furfuryl alcohol is 46.24%, 98.64%, 92.89%, 92.86% and 80.41%, respectively. It can be seen that the coordination type zirconium phosphotungstate catalyst prepared by the invention can achieve a high yield of furfuryl alcohol at 120° C. and react for 1 h.

EXAMPLE 6

(1) Weigh 200 mg of the coordination type zirconium phosphotungstate catalyst prepared in example 1 into 20 ml of polytetrafluoroethylene lining, and add quantitative naphthalene and 5 ml of isopropanol;

(2) Weigh 0.1 mol furfural and add it into the reaction system of step (1), put the PTFE lining into the stainless steel reaction kettle, heat it to 120° C. under magnetic stirring, react for 0.5-4 h, the reaction is finished, after the reaction kettle is cooled to room temperature, separate the solid and liquid with centrifuge, take the liquid phase as the sample to be tested;

(3) The reaction solution in step (2) of 50 μL was transferred with a pipette gun and the yield of furfuryl alcohol was determined by gas chromatography.

Figure 5:
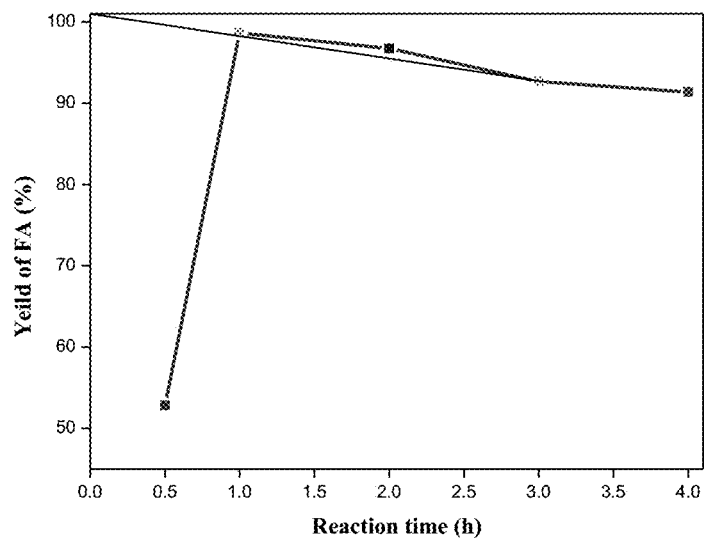
FIG. 5 shows the furfuryl alcohol yield of the coordinated zirconium phosphotungstate catalyst in example 6 under different time.

As shown in FIG. 5, the yield of furfuryl alcohol is 52.82%, 98.64%, 96.72%, 92.67% and 91.38% when the reaction time is 0.5 h, 1 h, 2 h, 3 h and 4 h respectively. It can be seen that with the increase of reaction time, the yield of furfuryl alcohol increases gradually, and then decreases.

EXAMPLE 7

(1) Weigh 100 mg, 150 mg, 200 mg, 250 mg or 300 mg of the coordination type zirconium phosphotungstate catalyst prepared in example 1 respectively into 20 ml of polytetrafluoroethylene lining, and add quantitative naphthalene and 20 ml of isopropanol;

(2) Weigh 0.1 mol furfural and add it into the reaction system of step (1), put the PTFE lining into the stainless steel reactor, heat it to 120° C. under magnetic stirring, react for 1 h, after the reactor cools to room temperature, use the centrifuge to separate the solid and liquid, take the liquid as the sample to be tested;

(3) The reaction solution in step (2) of 50 µL was transferred with a pipette gun and the yield of furfuryl alcohol was determined by gas chromatography.

Figure 6:
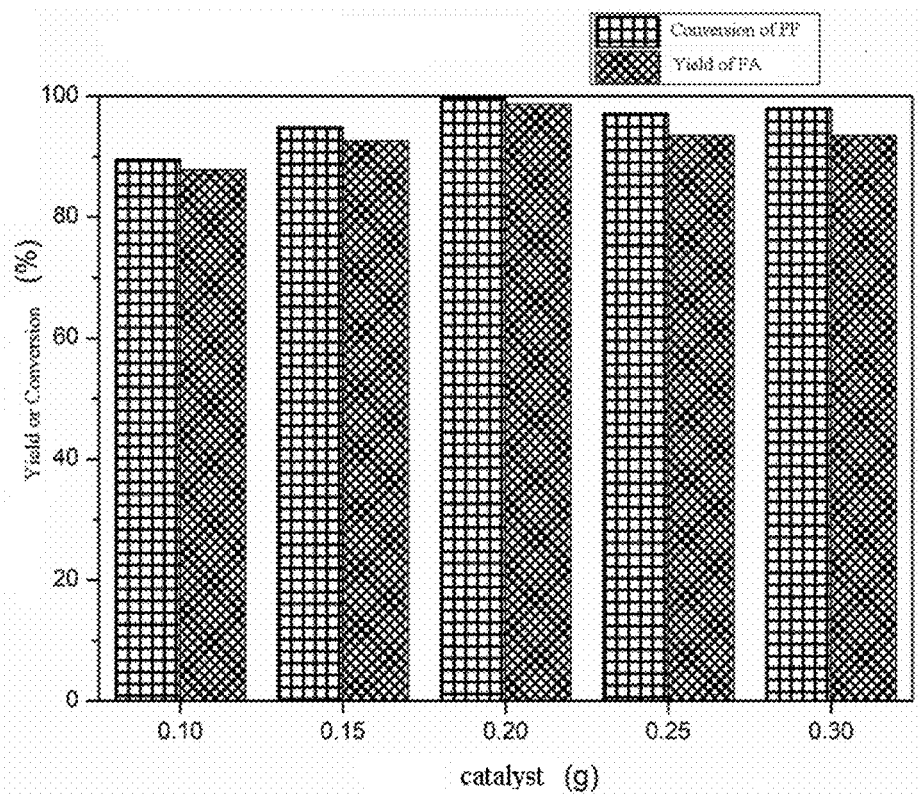
FIG. 6 shows the furfuryl alcohol yield of the coordinated zirconium phosphotungstate catalyst in Example 7 under different catalyst dosage.

As shown in FIG. 6, when the amount of catalyst is 100 mg, 150 mg, 200 mg, 250 mg and 300 mg respectively, the yield of furfuryl alcohol is 87.76%, 92.61%, 98.64%, 93.52% and 93.52% respectively.

EXAMPLE 8

(1) Weigh 200 mg of the coordination type zirconium phosphotungstate catalyst prepared in example 1 into 20 ml of polytetrafluoroethylene lining, add quantitative naphthalene, respectively add solvent methanol, ethanol, n-pentanol, n-butanol, 2-butanol and t-butanol;

(2) Weigh 0.1 mol furfural and add it into the reaction system of step (1), put the PTFE lining into the stainless steel reactor, heat it to 120° C. under magnetic stirring, and react for 1H. After the reactor cools to room temperature, use the centrifuge to separate the solid and liquid, and take the liquid as the sample to be tested;

(3) The reaction solution in step (2) of 50 µL was transferred with a pipette gun and the yield of furfuryl alcohol was determined by gas chromatography.

Figure 7:
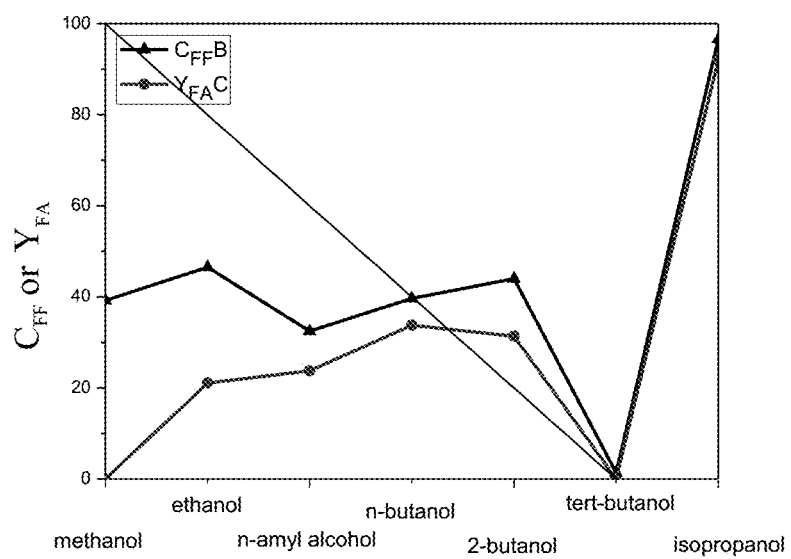
FIG. 7 shows the furfuryl alcohol yield of the coordinated zirconium phosphotungstate catalyst in example 8 under different reaction solvents.

As shown in FIG. 7, when the reaction solvent is methanol, ethanol, n-pentanol, n-butanol, 2-butanol and tert butanol, the yield of furfuryl alcohol is 0%, 21.08%, 23.75%, 33.75%, 31.35% and 0%, respectively.

EXAMPLE 9

(1) Weigh 200 mg of the coordination type zirconium phosphotungstate catalyst prepared in example 1 into 20 ml of polytetrafluoroethylene lining, and add quantitative naphthalene and 5 ml of isopropanol;

(2) Weigh 0.1 mol furfural and add it into the reaction system of step (1), put the PTFE lining into the stainless steel reactor, heat it to 120° C. under magnetic stirring, and react for 1H. After the reactor cools to room temperature, use the centrifuge to separate the solid and liquid, and take the liquid phase as the sample to be tested;

(3) The reaction solution in step (2) of 50 µL was transferred with a pipette gun and the yield of furfuryl alcohol was determined by gas chromatography.

After the reaction, clean and dry the filtered catalyst, and then put it into the above catalytic reaction for recycling. The results show that the yield of furfuryl alcohol is still as high as 82.44% after 6 cycles of use of coordination zirconium phosphotungstate.

Although the invention has been disclosed as above in a preferred embodiment, it is not used to define the invention. Anyone familiar with the technology can make various changes and modifications within the spirit and scope of the invention. Therefore, the scope of protection of invention shall be subject to that defined in the claims.

What is claimed is:

1. A method for preparing furfuryl alcohol by catalytic hydrogenation of furfural comprising hydrogenating the furfural in presence of the coordination zirconium phosphotungstate as a catalyst, wherein the method of making the coordination type zirconium phosphotungstate catalyst comprising: dissolving phosphotungstic acid and $ZrCl_4$ in DMF respectively to obtain phosphotungstic acid solution and $ZrCl_4$ solution; after ultrasonic treatment, adding phosphotungstic acid solution drop by drop into $ZrCl_4$ solution within 5-30 min;
   after uniform mixing, adding triethylamine; then reacting at room temperature for 3-6 hours; aging more than 4 hours; washing for 1-3 times with DMF, methanol, and anhydrous ether respectively;
   and drying in vacuum at 70-100° C. for more than 8 hours.

2. The method according to claim 1 wherein the hydrogenating is conducted in presence of isopropanol in an amount of 5-10 ml/mmol furfural as a hydrogen source.

3. The method according to claim 2 wherein the amount of isopropane is 5 ml/mmol furfural.

4. The method of claim 1 wherein the hydrogenating is conducted at a temperature of 120° C.

5. The method of claim 1 wherein the hydrogenating is conducted for 1 hour.

6. The method of claim 1 further comprising converting the furfuryl alcohol to resin, fuel, synthetic fiber, rubber, plastic, or pesticide.

7. The method of claim 1 wherein the hydrogenating is conducted in presence of 0.01-0.03 g coordination zirconium phosphotungstate/mmol furfural as the catalyst at 110-150° C. for 0.5-4 hours.

8. The method according to claim 1 wherein the molar ratio of the phosphotungstate and $ZrCl_4$ is 3:1~1:3.

9. The method according to claim 1 wherein the concentration of the phosphotungstate solution is (0.05-0.15) mol/L, and the concentration of the $ZrCl_4$ solution is (0.05-0.15) mol/L.

10. The method according to claim 1 wherein the ultrasonic treatment time is 5 to 30 minutes.

* * * * *